United States Patent
Bojovschi et al.

(10) Patent No.: US 9,652,841 B2
(45) Date of Patent: May 16, 2017

(54) SYSTEM AND METHOD FOR CHARACTERIZING NANO/MICRO BUBBLES FOR PARTICLE RECOVERY

(71) Applicant: International Business Machines Corporation, Armonk, NY (US)

(72) Inventors: Alexe Bojovschi, Melbourne (AU); Xi Liang, Altona Meadows (AU)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 14/797,348

(22) Filed: Jul. 13, 2015

(65) Prior Publication Data

US 2017/0011506 A1   Jan. 12, 2017

Related U.S. Application Data

(60) Provisional application No. 62/188,911, filed on Jul. 6, 2015.

(51) Int. Cl.
*G06T 7/00* (2006.01)
*G01N 33/566* (2006.01)
(Continued)

(52) U.S. Cl.
CPC ............ *G06T 7/0008* (2013.01); *A61L 15/42* (2013.01); *G01N 1/34* (2013.01); *G01N 13/00* (2013.01);
(Continued)

(58) Field of Classification Search
CPC ................ G06T 7/0008; G06T 7/0042; G06T 2207/30108; A61L 15/34; A61L 15/42;
(Continued)

(56) References Cited

U.S. PATENT DOCUMENTS

| | | | |
|---|---|---|---|
| 4,981,582 A * | 1/1991 | Yoon | B01F 5/0408 209/164 |
| 5,096,572 A | 3/1992 | Hwang | |

(Continued)

FOREIGN PATENT DOCUMENTS

| | | |
|---|---|---|
| CN | 201371078 Y | 12/2009 |
| CN | 101362118 B | 1/2012 |

(Continued)

OTHER PUBLICATIONS

Ahmed, Ahmed S. Sayed, "Cavitation Nanobubble Enhanced Flotation Process For More Efficient Coal Recovery", Theses and Dissertations-Mining Engineering, University of Kentucky, 2013, 169 pgs.

(Continued)

*Primary Examiner* — Manav Seth
(74) *Attorney, Agent, or Firm* — Harrington & Smith; Louis J. Percello

(57) ABSTRACT

A control system for a froth flotation system receives inputs from one or more sensors comprising images of a fluid having bubbles and particles therein; some of the bubbles are attached to some of the particles and suspended in the fluid. For at least some of the bubbles with attached particles, it is determined from the inputs at least two contact angles at different locations at which the respective bubble is attached to the particle. These contact angles are used to predict a process improvement by which bubbles would more efficiently float the particles out of the fluid, as compared to that represented by the input images. An output is then provided for driving a graphical display screen, the output comprising at least one of: a) a graphical representation of the determined at least two contact angles; and b) a graphical representation of the predicted process improvement.

18 Claims, 6 Drawing Sheets

(51) Int. Cl.
*G01N 1/34* (2006.01)
*A61L 15/42* (2006.01)
*G01N 13/00* (2006.01)
*G01N 15/14* (2006.01)
*G01N 35/10* (2006.01)

(52) U.S. Cl.
CPC ....... *G01N 15/1404* (2013.01); *G01N 33/566* (2013.01); *G06T 7/0042* (2013.01); *G01N 2035/1053* (2013.01); *G06T 2207/30108* (2013.01)

(58) Field of Classification Search
CPC .. G01N 33/566; G01N 13/00; G01N 15/1404; G01N 1/34; G01N 2035/1053
See application file for complete search history.

(56) References Cited

U.S. PATENT DOCUMENTS

| | | | |
|---|---|---|---|
| 5,397,001 A | 3/1995 | Yoon et al. | |
| 5,814,210 A | 9/1998 | Yoon et al. | |
| 6,090,294 A * | 7/2000 | Teran | C02F 1/78 210/141 |
| 6,234,318 B1 | 5/2001 | Breau et al. | |
| 6,776,292 B1 * | 8/2004 | Nenno | B03D 1/1462 209/168 |
| 6,778,881 B1 | 8/2004 | Du Plessis et al. | |
| 6,959,815 B2 * | 11/2005 | Xu | B03D 1/02 209/166 |
| 7,129,199 B2 * | 10/2006 | Zhang | G03F 7/0048 510/175 |
| 7,341,622 B2 * | 3/2008 | Takagi | D06P 5/30 106/31.27 |
| 7,417,099 B2 * | 8/2008 | Savu | B01F 17/0035 526/243 |
| 7,462,819 B2 * | 12/2008 | Smart | G01N 23/2258 250/282 |
| 7,591,452 B2 | 9/2009 | Kohama et al. | |
| 7,975,531 B2 * | 7/2011 | Nguyen | B01L 3/502784 356/244 |
| 8,114,221 B2 * | 2/2012 | Labib | B08B 9/032 134/22.1 |
| 8,201,439 B2 * | 6/2012 | Szabo | G01N 13/00 73/64.48 |
| 8,226,774 B2 * | 7/2012 | Labib | B08B 9/0325 134/22.11 |
| 8,753,497 B2 * | 6/2014 | Aubry | B03C 5/005 204/450 |
| 8,915,374 B2 * | 12/2014 | Franks | B01D 17/0202 209/166 |
| 9,046,641 B2 * | 6/2015 | Lai | G02B 1/043 |
| 2005/0053642 A1 * | 3/2005 | Ulbricht | A61L 27/34 424/443 |
| 2005/0076936 A1 * | 4/2005 | Pung | A47L 13/17 134/6 |
| 2006/0289740 A1 * | 12/2006 | Smart | H01J 49/0004 250/287 |
| 2007/0189972 A1 | 8/2007 | Chiba et al. | |
| 2014/0225416 A1 | 8/2014 | Harding et al. | |

FOREIGN PATENT DOCUMENTS

| | | |
|---|---|---|
| CN | 202129149 U | 2/2012 |
| CN | 104199389 A | 12/2014 |
| WO | 97/45203 A1 | 12/1997 |
| WO | 2014/188232 A1 | 11/2014 |

OTHER PUBLICATIONS

Clift, R., et al., "Bubbles, Drops, and Particles", Academic Press, 1978, 394 pgs.
Karpitschka, Stefan, et al., "Nonintrusive Opitcal Visualization of Surface Nanobubbles", Physical Review Letter (/PRL/), Amercian Physical Society, 2012, 2 pgs.
Poynor, Adele, et al., "How Water Meets a Hydrophobic Surface", Physical Review Letters, Dec. 31, 2006, 4 pgs.
Samet, Hanan, et al., "Efficient Component Labeling of Images of Arbitrary Dimension represented by Linear Bintrees", IEEE Transactions on Pattern, Analyses and Machines Intelligence, vol. 10, No. 4, Jul. 1988, 8 pgs.
Soni, Gaurav, "Development And Validation Of A Simulator Based On A First-Principle Flotation Model", Thesis, Virginia Polytechnic Institute and State University, Jun. 27, 2013, 58 pgs.
Steitz, Roland, et al., "Nanobubbles and Their Precursor Layer at the Interface of Water Against a Hydrophobic Substrate", American Chemical Society, 2003, pp. 2409-2418.
Wang, Yuliang, et al., "Boundary slip and nanobubble study in micro/nanofluidics using atomic force microscopy", Soft Matter (RSC Publishing), Issue 1, 2010, 5 pgs.
Zhang, Xh, et al., "A nanoscale gas state", Physical Review Letters, Mar. 30, 2007, 1 pg.
Zhou, et al., "Interaction of Ionic Species and Fine Solids with a Low Energy", Journal of Colloid and Interface Science, vol. 204, Issue 2, Aug. 1998, 1 pg.

\* cited by examiner contour 702 bounding box 704   centroid 704C

US 9,652,841 B2

SYSTEM AND METHOD FOR CHARACTERIZING NANO/MICRO BUBBLES FOR PARTICLE RECOVERY

PRIORITY CLAIM

This application claims priority under 35 USC §119(e) to provisional U.S. patent application Ser. No. 62/188,911, filed on Jul. 6, 2015, the contents of which is hereby incorporated by reference in its entirety.

TECHNICAL FIELD

The exemplary embodiments of this invention relate generally to characterizing and visualizing nano and/or micro bubbles as may be used in a particle recovery process which floats particles that attach to such bubbles out of a liquid, where this characterizing and visualizing is computer-driven and includes image processing.

BACKGROUND

The general concept of recovering or recycling particles out of a solution by bubbling the solution so as to float the particles to the surface is well known and used in a wide variety of industries, Commonly known as froth flotation, this is a process whereby hydrophobic particles come in contact with and adhere to bubbles, rising with them to the surface to form a froth as is generally shown at FIG. 1. Publication WO 2014/188232 describes using aerator injection nozzles to recover ore from a slurry or pulp containing water and fine ore particulates. Flotation efficiency has been shown to increase up to 20% percent in the presence of nano/micro bubbles, and while the specific mechanism is not clearly understood this efficiency improvement is considered to be due to nano/micro bubbles. In general for froth flotation separation, the hydrophobic particles bind to the surface of the fine bubbles and float while the hydrophilic particles remain as waste. Various reactants/chemical reagents can be added to the foam or froth flotation system to make the desired particles water repellant so as to bias their attachment to the bubble surfaces. Apart from ore recovery WO 2014/188232 describes how this process can be used to remove paint from recycled paper, oil and fat particles from food industry waste water, particulates in the recovery of contaminated sites, and for treating waste water produced by oil fields.

Further details concerning nano-bubble froth flotation industrial processes for efficient recovery of fine and course mineral, coal, oil sand and paper particles in mining and recycling industries can be seen in a document by S. Ahmed entitled *Cavitation nanobubbles enhanced flotation process for more efficient coal recovery* (PhD thesis, Kentucky University, 2013). Estimating adhesion of the bubbles to particle surfaces from contact angle measurements is explored in an article by S. R. Rao entitled *Surface Chemistry of Froth Flotation* (SPRINGER, Vol. 2, 2004). The above-referenced PhD thesis by S. Ahmed asserts that large-particle recovery technology is currently limited to about 100 micro-meters for minerals and 600 micro-meters for coal, but an article by A. Goodbody entitled *Staying the Coarse* (MINING MAGAZINE, November 2014) proposes that enabling flotation of coarse particles has the potential to reduce the energy in the froth flotation process chain with significant economic benefits.

Nano/micro-bubbles form naturally or can be generated artificially. Systems for generating nano and/or micro-bubbles are proposed in various publications including U.S. Pat. No. 7,591,452 and US patent application publication no. 2007/0189972; as well as papers by Z. Zhou, H. Hussein, Z. Xu, J. Czarnecki and J. H. Masliyah entitled *Interaction of ionic species and fine solids with low energy hydrophobic surface from contact Angle measurement* (JOURNAL OF COLLOID INTERF. SCI., Vol. 204, pp. 342-349, 1998); by R. Clift, J. R. Grace and M. E. Weber entitled *Bubbles, drops and particles* (ACADEMIC PRESS, 1978); and by H. Takushoku entitled *Progress in Chemical Engineering—Bubble, Drop, and Dispersion Engineering* (MAKI SHOTEN, 1982). The majority of these techniques are seen to generate nano-bubbles with a non-uniform size distribution, which can be fitted by a normal distribution. It appears to the inventors that the only known technique that produces micro/nano-bubbles with a relatively uniform size distribution is described in U.S. Pat. No. 7,591,452, which injects gas through a porous materials having similar-diameter pores. After the nano/micro-bubbles are injected they attach to particles or stay dispersed in the solution.

There are known methods used to provide a digital image of the nano/micro-bubbles under investigation. They include neutron reflectometry (Steitz, R., Gutberlet, T., Hauss, T., Klosgen, B., Krastev, R., Schemmel, S., Simonsen, A. C. and Findenegg, G. H., *Nanobubbles and Their Precursor Layer at the Interface of Water Against a Hydrophobic Substrate*, LANGMUIR, Vol. 19, pp. 2409-2418, 2003), X-ray reflectivity measurements (Poynor, A., Hong, L., Robinson, I. K., Granick, S., Zhang, Z. and Fenter, P. A., *How Water Meets a Hydrophobic Surface*, PHYS. REV. LETT. Vol. 97, pp. 266101-266104, 2006), optical spectroscopy (Zhang, X. H., Khan, A., and Ducker, W. A., *A Nanoscale Gas State*, PHYS. REV. LETT. Vol. 98, pp. 136101-136104, 2007), optical microscopy (Karpitschka, S., Dietrich, E., Seddon, J. R. T., Zandvliet, H. J. W., Lohse, D. and Riegler, H., *Nonintrusive Optical Visualization of Surface Nanobubbles*, PHYS. REV. LETT. Vol. 109, pp. 066102-066105, 2012) and tapping mode atomic force microscopy (Wang, Y., and Shushan, B., *Boundary slip and nanobubble study in micro/nanofluidics using atomic force microscopy*, SOFT MATTER, Vol. 6, pp. 29-66, 2010).

Previous computer vision studies in the flotation industry involved capturing images to assess froth characteristics such as mass, color and flow rate (Francois, E. Du P. and Marc, V. Olst, *Monitoring and control of a froth flotation plant*, 2004; and also international patent application publication WO 1997/045203), as well as particles and bubbles size, distribution and concentration (WO 1997/045203). All these parameters in the flotation cell are directly related with the grade and recovery efficiency of the foam/froth flotation system.

SUMMARY

In a first aspect thereof the embodiments of this invention provide an apparatus comprising one or more memories comprising computer-readable code and one or more processors. The one or more processors are configured, in response to execution of the computer-readable code, to cause the apparatus to perform actions comprising: receive inputs from one or more sensors, the inputs comprising images of a fluid having bubbles and particles therein, of which at least some of the bubbles are attached to some of the particles and suspended in the fluid; for at least some of the respective bubbles with attached particles, determine from the inputs at least two contact angles at different locations at which the respective bubble is attached to the particle; using the determined contact angles, predict a process improvement by which bubbles would more efficiently float the particles out of the fluid as compared to the input images; and provide an output for driving a graphical display screen, the output comprising at least one of: a) a graphical representation of the determined at least two contact angles; and b) a graphical representation of the predicted process improvement.

In yet another aspect thereof the embodiments of this invention provide a computer program product comprised a computer readable storage medium having program code embodied therewith. The program code is executable by a computing system to cause the computing system to perform: receiving inputs from one or more sensors, the inputs comprising images of a fluid having bubbles and particles therein, of which at least some of the bubbles are attached to some of the particles and suspended in the fluid; for at least some of the respective bubbles with attached particles, determining from the inputs at least two contact angles at different locations at which the respective bubble is attached to the particle; using the determined contact angles, predicting a process improvement by which bubbles would more efficiently float the particles out of the fluid as compared to the input images; and providing an output for driving a graphical display screen. The output comprises at least one of a) a graphical representation of the determined at least two contact angles; and b) a graphical representation of the predicted process improvement.

In another aspect thereof the embodiments of this invention provide a method comprising: receiving inputs from one or more sensors, the inputs comprising images of a fluid having bubbles and particles therein, of which at least some of the bubbles are attached to some of the particles and suspended in the fluid; for at least some of the respective bubbles with attached particles, determining from the inputs at least two contact angles at different locations at which the respective bubble is attached to the particle; using the determined contact angles, predicting a process improvement by which bubbles would more efficiently float the particles out of the fluid as compared to the input images; and providing an output for driving a graphical display screen. This output comprises at least one of: a) a graphical representation of the determined at least two contact angles; and b) a graphical representation of the predicted process improvement.

DETAILED DESCRIPTION

Figure 1:
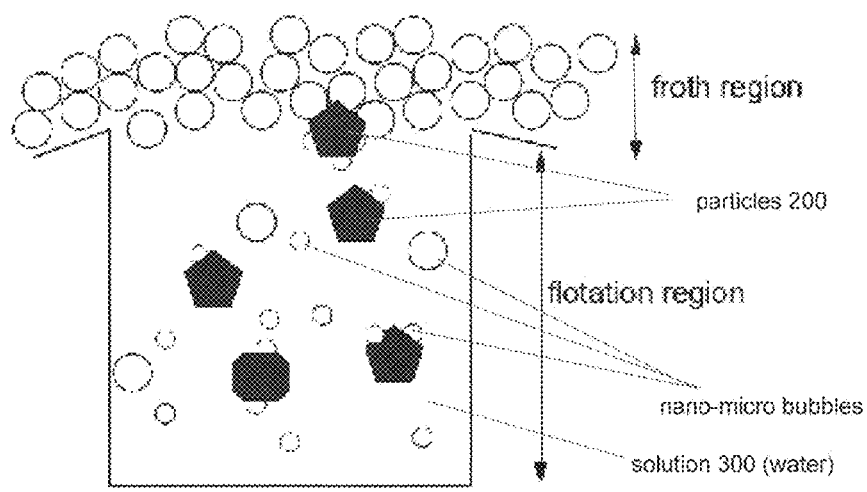
FIG. 1 is a sectional view of a flotation cell of a froth flotation system showing bubbles and particles attached to some of the bubbles.

A system capable of providing feedback into the recovery pipeline or other froth flotation system regarding the contact angle, size and distribution of nano/micro-bubbles in the flotation cell where particle recovery occurs has the potential to improve the particle/mineral recovery through a more controlled and optimized process. The ability of a froth flotation system to estimate the particle-bubble contact angle in real time would be beneficial, allowing a much more tailored use of surfactants or other chemical reagents and thereby improving efficiency and reducing cost. These are some advantages which are manifest in and realized by the embodiments described below.

Accurate tuning of bubble size and contact angle is important for increasing the probability and strength of the attachment between the bubbles and the particles. This attachment is described in part by the contact angle that is formed by the bubble 100 and its attached solid particle 200, shown schematically at FIG. 2. The liquid-side contact angle $\theta1$ is between the localized surface of the particle 100 and a tangent to its point of contact on the exterior surface of the bubble 200 and is more particularly detailed below for a specific embodiment with respect to FIG. 8, whereas the gas-side contact angle $\theta2$ is between the localized surface/sidewall of the particle 100 and the interior surface/sidewall of the bubble 200 (thus $\theta2=180-\theta1$). Controlling the contact angle through tailored use of a surfactant and/or other chemical reagents can optimize this attachment, and such optimization can aid in overcoming the deficiency noted in the above-referenced paper/thesis by S. Ahmed as to froth flotation of larger particles. Additionally, by more precisely controlling the contact angle it is possible to optimize the specific chemical reagents chosen for, and quantities thereof, use in a given froth flotation process in order to strengthen the bubble attachment as well as bias it more strongly to only the desired particles Example embodiments of the invention described herein provide a method for automated characterization of surface and bulk nano/micro-bubbles. As detailed further herein, this allows real time information to be obtained as to the nano/micro-bubble size as well as the relevant contact angle values and distribution. Such example embodiments may be manifested as computer vision systems and image processing methods used for froth flotation, as well as the process and apparatus (e.g., a computer control system for a froth flotation system and/or components thereof such as the aerator injection and/or surfactant subsystems) that allows predicting and improving the particle recovery efficiency through nano/micro-bubble characterization.

The paper by Ahmed referenced in the background section above suggests that improving the probability of bubble-particle interaction can be achieved through an increase in the density of bubbles. Adhesion of a specific size bubble to the desired particle can be facilitated by finely controlling the bubble size distribution and the contact angle, and optimizing the froth flotation process in this manner can be done simultaneously with increasing the bubble density per the paper by Ahmed. The information obtained by characterizing the contact angle and nano/micro bubble size distribution according to the techniques described herein can be used to optimize the flotation process by adjusting the number and size of gas bubbles generated. Additionally, monitoring the condition of the bubble generating devices can be provided based on the number density of nano/micro bubbles. Such bubble generating devices in the context of a froth flotation system are referred to herein as the aeration injector system, regardless of whether air or some other gas is being injected.

Figure 3:
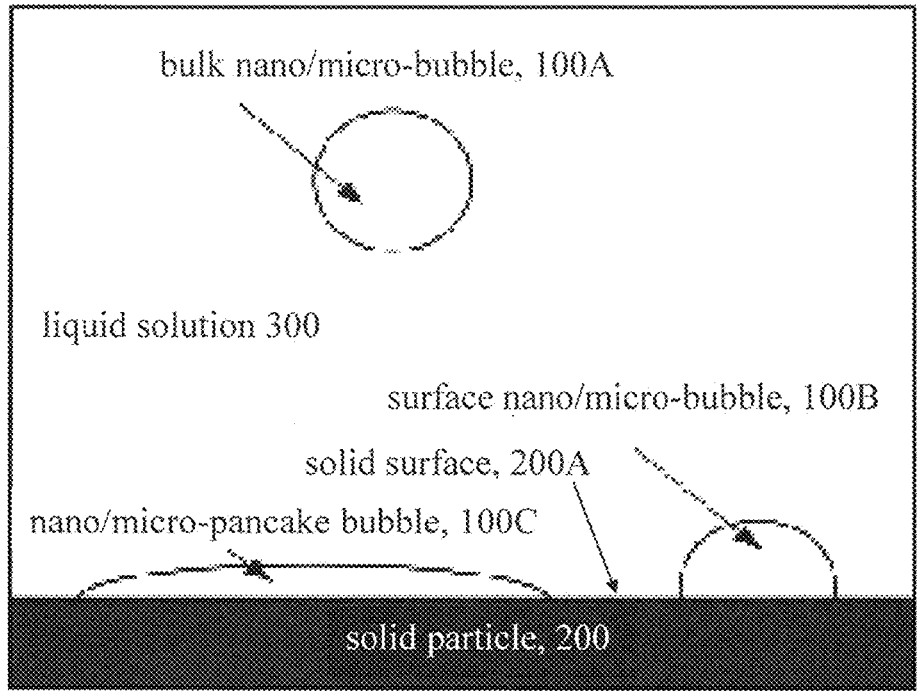
FIG. 3 represents an image illustrating three type of micro/nano gaseous domains in a pulp suspension and this image is segmented when visualizing the flotation process according to embodiments of these teachings.

Accurate characterization and visualization of these bubbles and specifics of the particles' attachment thereto enables more effective adjustments towards optimizing such particle recovery processes. As an initial matter for this characterization and visualization, first an image of the bubbles in the pulp suspension is taken. The pulp is the liquid with the particles to be frothed out, and as noted in the background section there is a variety of known techniques to take such an image. In fact the process described herein for characterizing and visualizing an operational froth flotation system would be ongoing and dynamic so there would be a continuous stream of real-time images which are processed sequentially or by groups in parallel, but for clarity of explanation consider how a single image is handled. An image processing procedure according to embodiments of these teachings then separates that image of the bubbles in pulp suspension into at least three parts: air (gas or bubbles), liquid and solid. FIG. 3 shows such separation with a layer of solid particles 200 along the bottom, bubbles 100 of various types 100A, 100B, 100C, and the liquid solution 300 which is shown as the unshaded background. Bubbles 100 that are enclosed within liquid and in contact with a solid surface 200A, such as a layer of particulates that are settled along the bottom of the aeration/flotation chamber and shown as both surface nano/micro bubble 100B and nano/micro-pancake bubble 100C, are also considered when separating the image into the gas, liquid and solid parts. It is convenient to first separate liquid 300 from solid 200 in this image. Both liquid 300 and solid 200 can be considered as connected components and so they are relatively simpler to segment from the image. Generally the nano/micro-bubbles 100 within the liquid 300 are separated from each other, so these can be separated from the liquid 300 after the liquid 300 is segmented from the solid 200.

Various segmentation methods can be applied to separate the air bubbles 100), liquid 300 and solid 200 components. As one example, first assume that the relative magnitude of the intensity of the different components in the image is that air is the least intense, solid 200 is the most intense, and liquid 300 is between them (e.g., air<liquid<solid). This assumption allows us to apply a multi-threshold method as follows. Let I(x,y) be the intensity of pixels at location (x,y) of the image. The pixels of the three different components in the image are identified as:

air$(x,y)=\{x,y|I(x,y)<$threshold_1$\}$ liquid$(x,y)=\{x,y|$threshold_1$<=I(x,y)<$threshold_2$\}$ solid$(x,y)=\{x,y|I(x,y)>=$threshold_2$\}$ Another example can be based on the assumption that air 100, liquid 300 and solid 200 are connected components. In this case for the correctly oriented image air is located at the top (e.g., the froth region at FIG. 1), solid 200 is located at the bottom and liquid 300 is located in between. The components can be separated using an active contour method or via region growing using seeds that are located on the top, middle and bottom of the image. Further particulars of a suitable region-growing method can be seen in the textbook *Image Processing the Fundamentals* by M. Petrou and P. Bosdogianni (WILEY, UK; 2004).

In the solution, we segment the nano/micro-bubbles and assign an ID to each bubble. There are various segmentation methods that can be used to segment bubbles in an image series. For example, in one technique after the nano/micro-bubbles 100 have been segmented, each individual bubble is assigned with a unique identifier ID. One specific technique to assign such IDs is to use connected component labeling to identify all isolated regions. Particulars on such connected component labeling can be seen in an article by H. Samet and M. Tamminen entitled *Efficient Component Labeling of Images of Arbitrary Dimension Represented by Linear Bintrees* (IEEE TRANSACTIONS ON PATTERN ANALYSIS AND MACHINE INTELLIGENCE, Vol. 10, pp. 579; 1988). Using this labeling technique for the relevant images of bubbles in the pulp suspension, each isolated region of the image would be a bubble, and according to these teachings each isolated region would then be assigned with a unique ID. For each bubble, the volume or size is computed. As one non-limiting example, the volume can be computed by multiplying the total number of pixels in the bubble with the pixel size (e.g., total pixel number*pixel size=bubble volume).

Based on this computed volume or size of bubbles, now the distribution of the bubbles can be plotted. The size of the nano/micro-bubble is important for enhancing flotation of the desired particles because bubbles of different sizes have different functionality (e.g., bubble size relates to the size/mass of particles it can effectively attach to and float). The bubble size is also an important indicator of the nano/micro bubble stability. In certain embodiments of these teachings the processing software classifies the bubbles in a given image into the three types shown at FIG. 3: bulk nano/micro-bubbles 100A, surface nano/micro-bubbles 100B and nano-pancakes 100C. The bubbles 100A in solution and the bubbles 100B, 100C attached on the surface 200A are classified. Based on the segmentation of the bubble types (bulk, surface and pancake), we compute the size distribution of the bubbles in each category/type.

Figure 4:
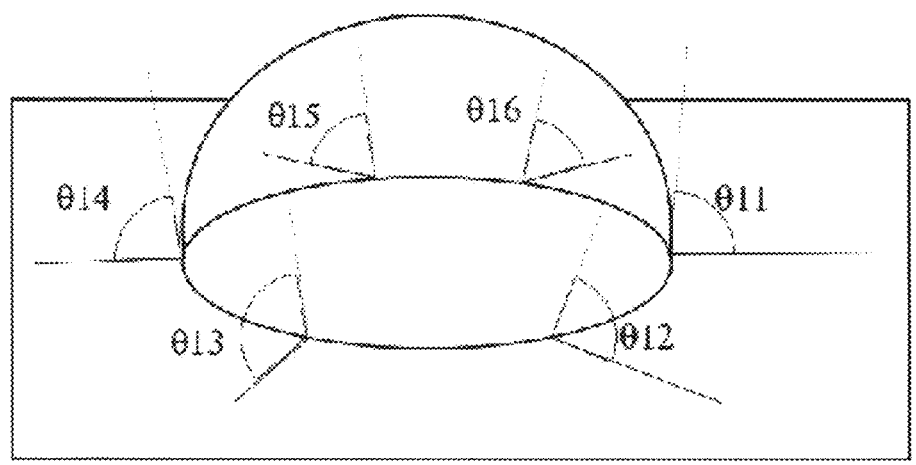
FIG. 4 is a diagram of a bubble/particle interface showing six liquid-side contact angles derived from interpolating among multiple images taken in a flotation chamber from multiple angles.

In a preferred embodiment the contact angle of gas domains are determined from interpolating images taken from multiple angles (two or three angles for example). The contact angle is estimated following a procedure best illustrated at FIGS. 4 and 5. FIG. 3 is an individual image from which contact angles in two dimensions as in FIG. 2 may be obtained. Repeating this for multiple images from multiple angles, and then interpolating from them, enables one to construct a better visualization of contact angles about the entire bubble/particle interface as shown at FIG. 4 which illustrates six such contact angles. The particle itself in FIG. 4 is not shaded so as to more clearly illustrate the liquid-side contact angles but the reader will understand that the vertex of these angles define the bubble/particle/liquid interface.

These contact angle values may then be used to optimize the flotation process, for example by more precisely metering the amount of surfactant introduced in the flotation cell or by adjusting the size of bubbles that the aerator injection system introduces to the liquid.

Figure 5:
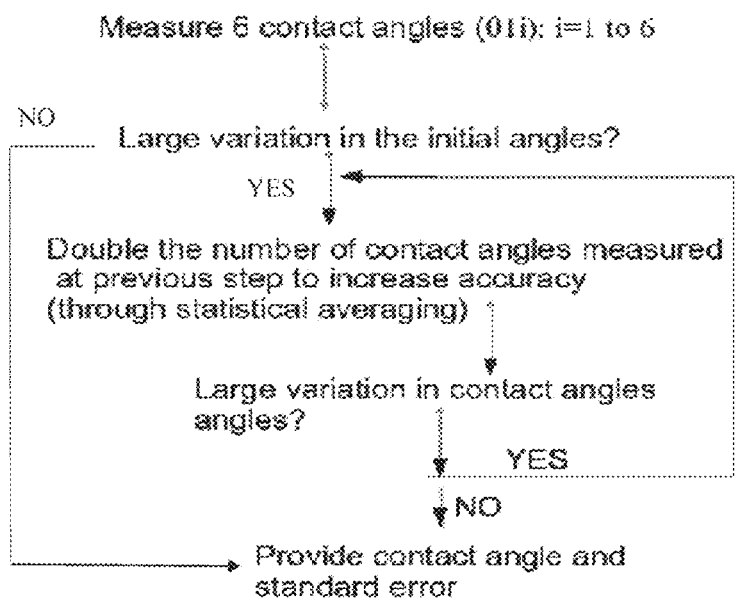
FIG. 5 is a process flow diagram for detecting large variations in the measurements of contact angles at the interface of a bubble and a particle, according to an exemplary embodiment of these teachings.

FIG. 5 is a process flow diagram for detecting large variations in contact angle measurements and improve estimation, and is one exemplary algorithm by which a software program may implement a portion of these teachings. Assuming we begin with an initial measure of six contact angles (and these measurements can be actual angles measured from images or angles extrapolated from multiple images), first it is checked how much variation there is among these six angles. This variation test can for example be whether the largest and smallest angle are within a threshold difference of one another, or the largest difference between any two adjacent angles are within a threshold difference, or it may be a distribution test to ensure all the angle sizes relative to one another lie within a maximum distribution curve. If this variation test is satisfied the NO branch from the initial angle variation test at FIG. 5 outputs the contact angle and standard error drawn from those six initial angles, otherwise FIG. 5 enters the iterative phase where the number of angles previously considered in the variation test is doubled and that doubled number of angles is subjected to the variation test. The additional angles may be taken from other images at different angles which is preferred for improved precision, or they may arise from further extrapolations, or some combination of both. This process repeats until the variation test is satisfied, in which case the output from FIG. 5 is a single contact angle with a standard error rate.

Figure 6:
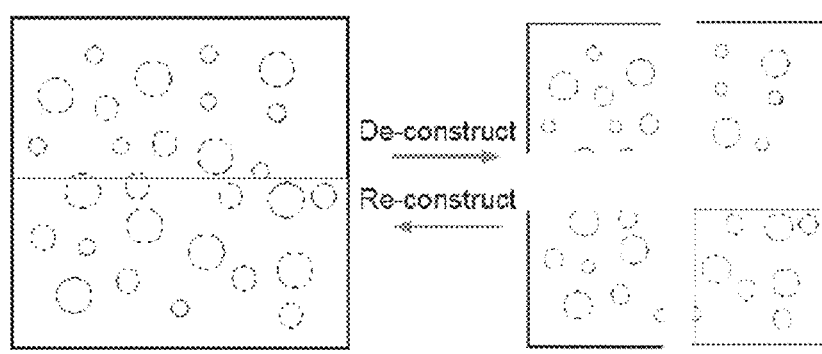
FIG. 6 is a diagram illustrating de-construction and re-construction of the digital image of bubbles for the case that a distributed computing platform is used to perform image processing according to an embodiment of these teachings.

In practice a given implementation of these teachings may entail high computational complexity, or there may be a large number of distinct flotation cells of a given froth flotation system that are being monitored and visualized for optimization. In these cases it may be more suitable to use distributed computing to perform the image processing in real time. This option may also be advantageous if a given computing platform is being used to monitor and visualize multiple different froth flotation systems in parallel. Any of these distributed computing cases can utilize image deconstruction and/or image reconstruction to exploit the advantages of distributed computing. For image deconstruction which FIG. 6 illustrates from left to right, the individual images are parsed so that each different grid resource is processing only a portion of the entire image taken by the camera or other sensor. Or alternatively the different grid resources can each process full images individually, with some images being processed by multiple grid resources as a continuing internal quality control to ensure the identical images yield similar results from different grid resources. FIG. 6 illustrates image reconstruction from right to left, and is used to combine the results from different grid resources so as to yield the final visualization showing representative bubble sizes and their representative contact angles with the liquid and particles. The individual results from the different grid resources may each represent a parsed portion of an image for which other grid resources processed the other portions, or a whole image, or all images from an individual flotation chamber that is not being processed by other grid resources, and so forth.

Figure 7A:
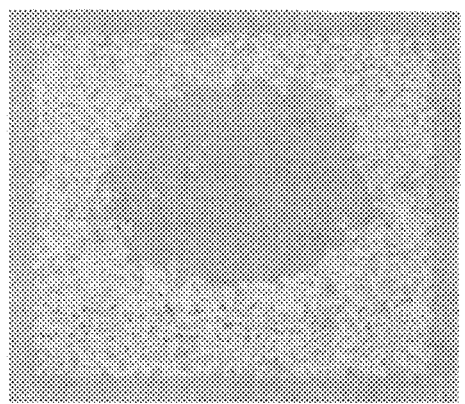
FIGS. 7A-D illustrate different steps in processing an image of a single neon-bubble using the region grow method, in order to characterize it for visualization according to embodiments of the teachings herein.
Figure 7B:
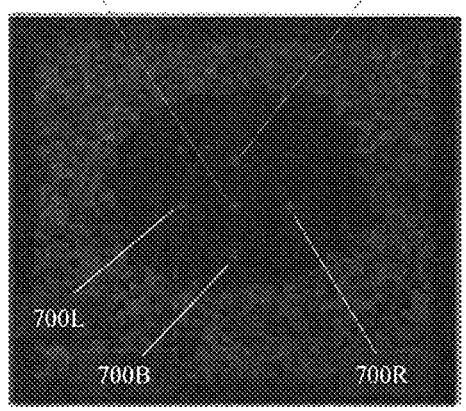
Figure 7C:
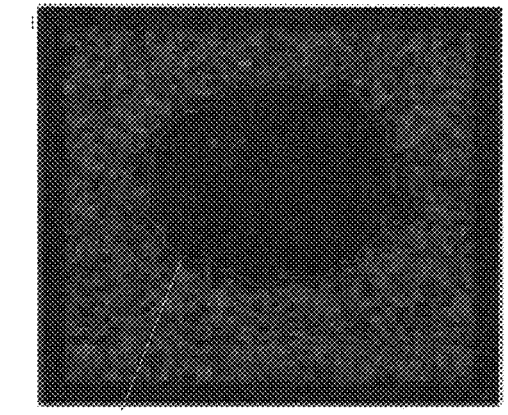
Figure 7D:
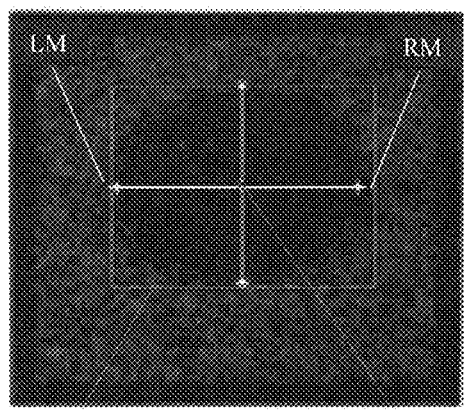
Figure 8:
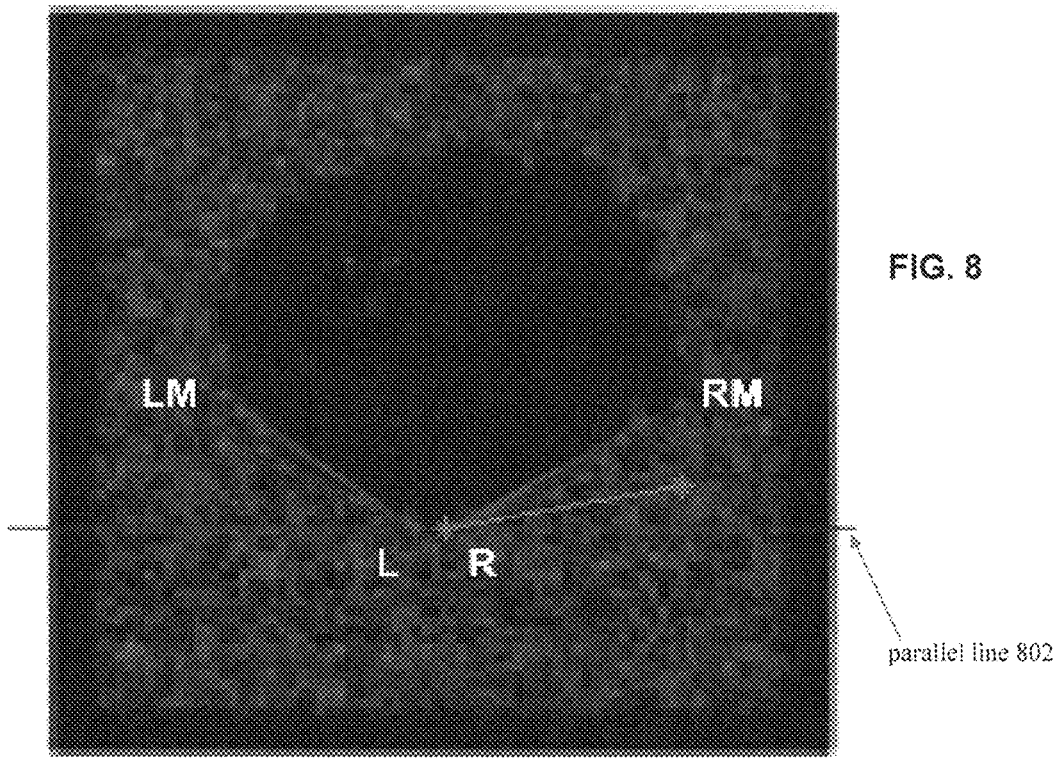
FIG. 8 is an illustration of the bubble characterized at FIGS. 7A-D and illustrates how the contact angles are computed according to an embodiment of these teachings.

To more fully illustrate the image processing involved, FIGS. 7 and 8 show steps in processing an image of an individual bubble using the region growing technique detailed in the above-mentioned textbook *Image Processing the Fundamentals*. Keep in mind the purpose of this processing is to enable one to compute geometrical parameters and the contact angle of nano/micro bubbles that are attached to a particle in the froth flotation system. In the pre-processing done prior to what is shown at FIGS. 7 and 8, the bubble image was converted to a gray-value image and re-sampled to ⅒ of the original size in both x and y Cartesian directions to reduce the computational cost. The region grow method employed for the FIG. 7-8 illustrations used five seeds shown at FIG. 7B, which include the center point 700C and four points located 10 pixels above 700A, below 700B, on the right 700R and on the left 700L of the center. The bubble is assumed to be located approximately at the center of the image.

The region, with 5 initial seed points, is iteratively grown by first comparing all unallocated neighboring pixels and then selectively including relevant pixels to the current region. The difference between the intensity of the pixels and the mean value of the region is used as a measure of contrast. The pixel with the smallest difference is allocated to the bubble. The process terminates when the intensity difference between the region mean and new pixel becomes larger than a certain threshold. A morphological closing is then applied on the generated bubble mask to fill all holes and smooth the boundary. The contour 702 of the bubble segmentation is obtained and is shown in FIG. 7C. Then a bounding box 704 shown at FIG. 7D, of the bubble defined by the contour 702, is computed as the minimum rectangle enclosing the bubble. The next step involves computing the bubble centroid 704C. The equatorial and polar lines through that centroid 704 that are shown in FIG. 7D intersecting in the center of the bubble are used to compute the axial parameters.

Now with the nano-bubble now mathematically characterized we can calculate the contact angles. In the technique that FIG. 8 illustrates for doing so, first a line 802 is constructed parallel to the particle surface which approximates a tangent line to the nano-bubble. The bubble shown in FIG. 8 is of the bulk type (see FIG. 3) and so there is no attached particle but the process is simpler for surface or pancake type bubbles. In the case of FIG. 8 since there is no attached particle the line 802 is drawn parallel to the equatorial axis of FIG. 7D for purposes of explanation, and so the respective points LM and RM are the same in FIG. 8 as in FIG. 7D.

The contact angle algorithm extracts the leftmost and rightmost points that are located both on the line 802 (point LM and RM) and the bubble (points L and R). Two curve intervals are then determined on the boundary/contour of the bubble. One curve interval starts from point L on the line 802 and extends to the leftmost point LM of the bubble boundary, and the other curve interval starts from point R on the line 802 and extends to the rightmost point RM of the bubble boundary. On each side, multiple points on each these curves are connected with the corresponding L or R on the line 802 (note that L and R also lie on the bubble surface) to form multiple line segments. The smallest angle between the line segments and the horizontal line 802 is defined as the contact angle on that side. The contact angles between the bubbles and the particle surfaces were estimated by averaging 4 angles from two orthogonal planes of density profiles that are perpendicular to the x and y axis respectively (FIG. 8).

Figure 9:
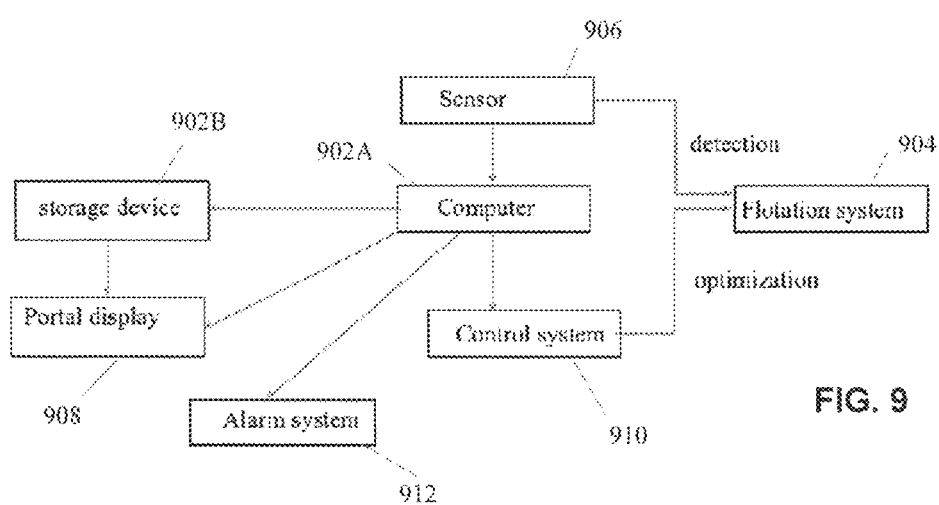
FIG. 9 is a high level block diagram showing a computing system for performing functions according to these teachings in association with a froth flotation system and various subsystems including sensors, controls and alarms

FIG. 9 is a high level block diagram showing a computing system in association with a froth flotation system and various subsystems including sensors, controls and alarms. Specifically the computing system includes a computer 902A representing one or more processors, and a storage device 902B which may be internal of the computer 902A or separate as shown, or there may be multiple memories storing the implementing computer-readable code and results of the implementing image processing software. The computer 902A interfaces with the flotation system 904, which has the flotation cell(s) holding the fluid with entrained bubbles and particles, via one or more sensors 906 such of various types detailed above by non-limiting example. The computer 8902A takes inputs from the sensor(s) 906 and provides outputs to a portal display 908 such as graphical display interface/display panel. The data is image processed in the computing device 902A/902B to identify parameters such as nano/micro-bubble distribution, volume and contact angle. The information is used by one or more micro-controllers in the flotation system's control system 910 to optimize the amount of surfactant injected into the flotation cell, and/or the volume and size of bubbles injected there. The obtained information can be displayed on a visualization device 908 or stored in the memory 902B for later use. In one embodiment the computer 902A automatically directs the control system 910 to make adjustments to implement the predicted optimization, and in another it outputs to the display 908 information about the predicted process improvement for implementation manually by a human operator. But these are not mutually exclusive; some suggested process improvements may be implemented automatically while others require manual intervention or an autonomous robotic system capable of performing the required task.

Additionally or alternatively, in one embodiment the described computer system 902A/902B can be used to detect faults in the gas injection system by providing notification to operators, such as for example via short-message-service SMS, or via email, automated phone call to a central operation unit, or sounding an alarm when conditions are detected beyond some pre-defined alarm threshold. This is indicated at FIG. 9 as the alarm system 912. The decision would be based on the real time data processing and anomaly detection regarding the gas nano/micro-bubble density and injection rate.

Figure 2:
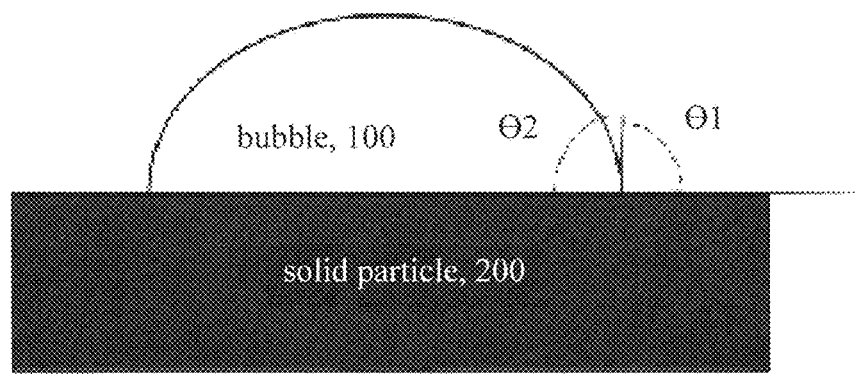
FIG. 2 is an expanded sectional view of an individual bubble with an attached particle, and showing liquid-side and gas-side contact angles between the gas bubble and a solid surface of the particle.
Figure 10:
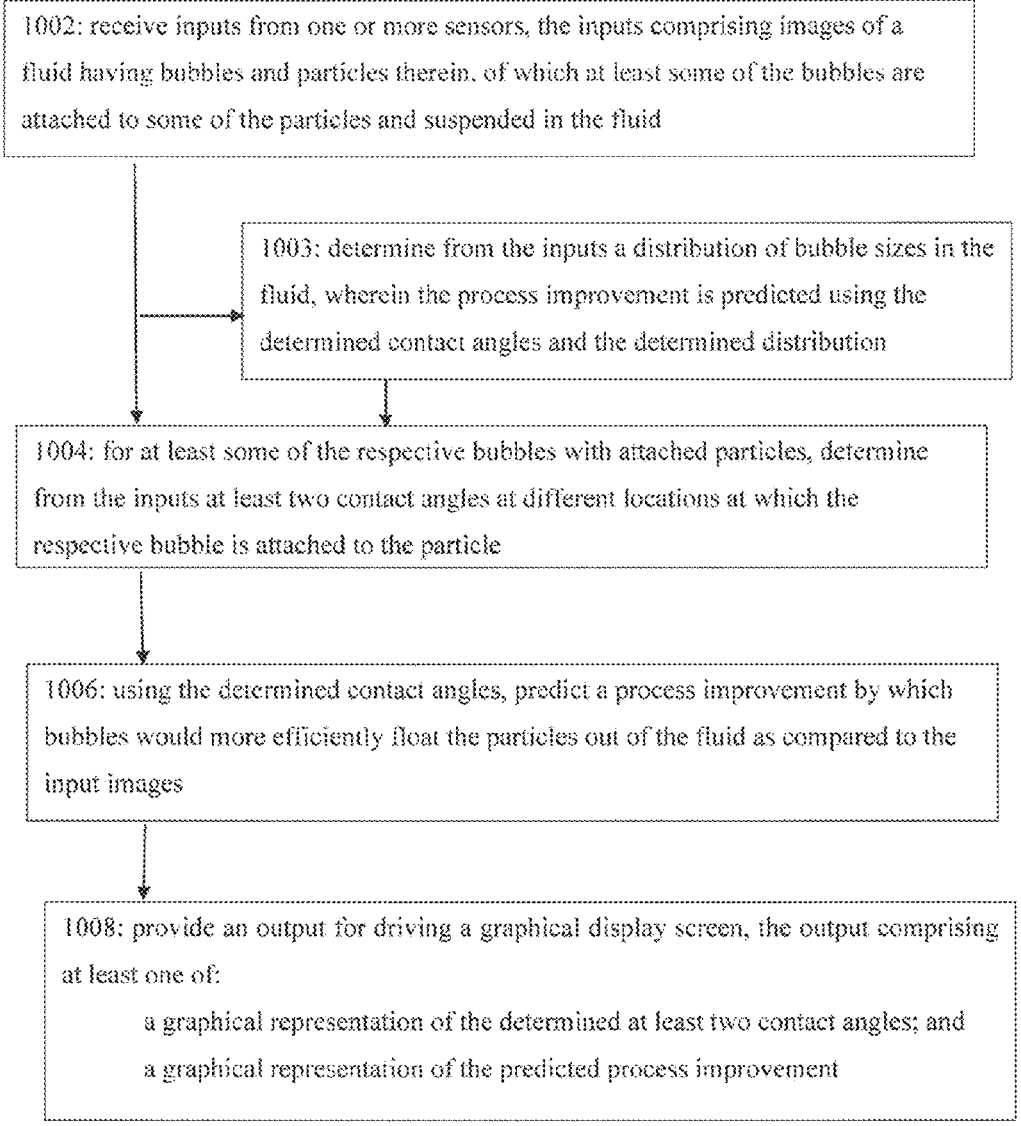
FIG. 10 is a logic flow diagram illustrating a method that encompasses certain features of the embodiments of this invention.

FIG. 10 is a logic flow diagram, also referred to as a flow chart, which illustrates a method encompassing certain features of the embodiments of this invention that are detailed more fully above. FIG. 10 may be implemented by an apparatus such as a computing system that includes one or more memories comprising computer-readable code and one or more processors, wherein the one or more processors are configured, in response to execution of the computer-readable code, to cause the apparatus to perform the actions shown at FIG. 7. At block 1002 the apparatus receives inputs from one or more sensors, where the inputs comprising images of a fluid having bubbles and particles therein, of which at least some of the bubbles are attached to some of the particles and suspended in the fluid. FIG. 3 is an example of such an input image and FIG. 4 is an example of an attached bubble/particle combination. For at least some of the respective bubbles with attached particles, block 1004 determines from the inputs at least two contact angles at different locations at which the respective bubble is attached to the particle. Then at block 1006 a process improvement is predicted, using the determined contact angles, by which bubbles would more efficiently float the particles out of the fluid as compared to the input images. Block 1008 concerns the graphical display, namely an output for driving a graphical display screen is provided and that output comprises at least one of a graphical representation of the determined at least two contact angles; and a graphical representation of the predicted process improvement. FIGS. 2 and 4 are examples of how the former might be displayed and FIG. 1 is an example of how the latter might be displayed, such as a video output showing the particles floating towards the top of the fluid at a rate commensurate with the predicted process improvement.

In certain embodiments also from the inputs of block 1002 there is determined a distribution of bubble sizes in the fluid as shown at block 1005. In this case then the process improvement is predicted using the determined contact angles of block 1004 and the determined distribution of block 1005. Non-limiting examples of the process improvements that can be predicted from a better knowledge of the contact angles (and bubble size distribution) includes changing size of bubbles injected into the fluid, changing concentration of bubbles injected into the fluid, and changing contact angles between bubbles and particles by adjusting concentration of a surfactant added to the fluid.

In the example above with respect to FIGS. 7A-D and 8, the contact angles of block 1004 were determined by comparing relative pixel intensity, which was used to segment each of the input images into solid, liquid and gas regions. In that specific example, each bubble within any of the gas regions is assigned a unique identifier, and a calculated bubble volume is stored in the apparatus'/computing system's memory in association with each of the unique identifiers. And as shown in FIG. 3 each bubble in the gas region is characterized as either a bulk bubble, a surface bubble or a pancake bubble.

Due to the high processing load associated with certain implementations of the image processing described herein, the implementing apparatus/computing system can comprise a grid computing system in which each node of the grid computing system comprises a respective memory and processor. As described with reference to FIG. 6, wherein at least some of the images of the fluid from block 1002 are deconstructed for processing at different ones of the nodes and the contact angles from block 1004 are determined after reconstructing the deconstructed images following this node-wise processing.

In order to more accurately assess the bubble's attachment to the particle and the angles that characterize this attachment, preferably the inputs of block 1002 are received from multiple sensors, and for at least some of the bubbles contact angles are determined from multiple images of the respective bubble taken from different angles.

The present invention may be implemented as a system, a method, and/or a computer program product. The computer program product may include a computer readable storage medium (or media) having computer readable program instructions stored thereon for causing a processor to carry out certain aspects of the present invention.

The computer readable storage medium such as the memory 902B can be a tangible device that can retain and store instructions for use by an instruction execution device (such as the data processor(s) of the computer 902A). The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As such, various modifications and adaptations may become apparent to those skilled in the relevant arts in view of the foregoing description, when read in conjunction with the accompanying drawings and the appended claims. As but some examples, the use of other similar or equivalent vulnerability types may be used by those skilled in the art. However, all such and similar modifications of the teachings of this invention will still fall within the scope of this invention.

What is claimed is:

1. An apparatus comprising:
   one or more memories comprising computer-readable code and one or more processors, wherein the one or more processors are configured, in response to execution of the computer-readable code, to cause the apparatus to perform actions comprising:
   receive inputs from one or more sensors, the inputs comprising images of a fluid having bubbles and particles therein, of which at least some of the bubbles are attached to some of the particles and suspended in the fluid;
   for at least some of the respective bubbles with attached particles, determine from the inputs at least two contact angles at different locations at which the respective bubble is attached to the particle;
   using the determined contact angles, predict a process improvement by which bubbles would more efficiently float the particles out of the fluid as compared to the input images, wherein the predicted process improvement is selected from the group comprising:
   changing size of bubbles injected into the fluid;
   changing concentration of bubbles injected into the fluid; and
   changing contact angles between bubbles and particles by adjusting concentration of a surfactant added to the fluid;
   and
   provide an output for driving a graphical display screen, the output comprising at least one of:
   a graphical representation of the determined at least two contact angles; and
   a graphical representation of the predicted process improvement.

2. The apparatus according to claim 1, the actions further comprising determine from the inputs a distribution of bubble sizes in the fluid, wherein the process improvement is predicted using the determined contact angles and the determined distribution.

3. The apparatus according to claim 1, wherein the at least two contact angles are determined from the inputs by comparing relative pixel intensity to segment each of the input images into solid, liquid and gas regions.

4. The apparatus according to claim 3, wherein each bubble within the gas regions is assigned a unique identifier, and a calculated bubble volume is stored in the memory in association with each of the unique identifiers.

5. The apparatus according to claim 3, wherein each bubble in the gas region is characterized as either a bulk bubble, a surface bubble or a pancake bubble.

6. The apparatus according to claim 1, wherein the apparatus comprises a grid computing system in which each node of the grid computing system comprises a respective memory and processor, wherein:
   at least some of the images of the fluid are deconstructed for processing at different ones of the nodes and
   the at least two contact angles are determined after reconstructing the deconstructed images after said processing.

7. The apparatus according to claim 1, wherein the inputs are received from multiple sensors, and for at least some of the bubbles at least two contact angles are determined from multiple images of the respective bubble taken from different angles.

8. A computer program product comprising a computer readable storage medium having program code embodied therewith, the program code executable by a computing system to cause the computing system to perform:
   receiving inputs from one or more sensors, the inputs comprising images of a fluid having bubbles and particles therein, of which at least some of the bubbles are attached to some of the particles and suspended in the fluid;
   for at least some of the respective bubbles with attached particles, determining from the inputs at least two contact angles at different locations at which the respective bubble is attached to the particle;
   using the determined contact angles, predicting a process improvement by which bubbles would more efficiently float the particles out of the fluid as compared to the input images, wherein the predicted process improvement is selected from the group comprising:
   changing size of bubbles injected into the fluid;
   changing concentration of bubbles injected into the fluid; and
   changing contact angles between bubbles and particles by adjusting concentration of a surfactant added to the fluid;
   and
   providing an output for driving a graphical display screen, the output comprising at least one of:
   a graphical representation of the determined at least two contact angles; and
   a graphical representation of the predicted process improvement.

9. The computer program product according to claim 8, wherein the program code executable by a computing system is further to cause the computing system to determine from the inputs a distribution of bubble sizes in the fluid, wherein the process improvement is predicted using the determined contact angles and the determined distribution.

10. The computer program product according to claim 8, wherein the at least two contact angles are determined from the inputs by comparing relative pixel intensity to segment each of the input images into solid, liquid and gas regions.

11. The computer program product according to claim 10, wherein each bubble within the gas regions is assigned a unique identifier, and a calculated bubble volume is stored in the storage medium in association with each of the unique identifiers.

12. The computer program product according to claim 10, wherein each bubble in the gas region is characterized as either a bulk bubble, a surface bubble or a pancake bubble.

13. The computer program product according to claim 8, wherein the inputs are received from multiple sensors, and for at least some of the bubbles the at least two contact angles are determined from multiple images of the respective bubble taken from different angles.

14. A method comprising:
   receiving inputs from one or more sensors, the inputs comprising images of a fluid having bubbles and particles therein, of which at least some of the bubbles are attached to some of the particles and suspended in the fluid;
   for at least some of the respective bubbles with attached particles, determining from the inputs at least two contact angles at different locations at which the respective bubble is attached to the particle;

using the determined contact angles, predicting a process improvement by which bubbles would more efficiently float the particles out of the fluid as compared to the input images, wherein the predicted process improvement is selected from the group comprising:

changing size of bubbles injected into the fluid;

changing concentration of bubbles injected into the fluid; and changing contact angles between bubbles and particles by adjusting concentration of a surfactant added to the fluid;

and providing an output for driving a graphical display screen, the output comprising at least one of:

a graphical representation of the determined at least two contact angles; and a graphical representation of the predicted process improvement.

15. The method according to claim 14, further comprising determining from the inputs a distribution of bubble sizes in the fluid, wherein the process improvement is predicted using the determined contact angles and the determined distribution.

16. The method according to claim 14, wherein the at least two contact angles are determined from the inputs by comparing relative pixel intensity to segment each of the input images into solid, liquid and gas regions.

17. The method according to claim 14, wherein the method is performed by a grid computing system in which each node of the grid computing system comprises a respective memory and processor, the method further comprising:

deconstructing at least some of the images of the fluid and distributing the deconstructed images among different ones of the nodes for processing; and reconstructing the deconstructed images after said processing, wherein the at least two contact angles are determined after the reconstructing.

18. The method according to claim 14, wherein the inputs are received from multiple sensors, and for at least some of the bubbles the at least two contact angles are determined from multiple images of the respective bubble taken from different angles.

* * * * *